United States Patent [19]

Schaaf

[11] Patent Number: 4,758,435

[45] Date of Patent: Jul. 19, 1988

[54] ESTRADIOL IMPLANT COMPOSITION AND METHOD FOR PREPARATION

[75] Inventor: Mimi Y. C. Schaaf, Princeton, N.J.

[73] Assignee: American Cyanamid Company, Stamford, Conn.

[21] Appl. No.: 895,415

[22] Filed: Aug. 11, 1986

[51] Int. Cl.⁴ .................. A61M 7/00; A61K 9/00; A61K 31/56

[52] U.S. Cl. .................................. 424/425; 514/182

[58] Field of Search ........................................ 424/425

[56] References Cited

U.S. PATENT DOCUMENTS 3,773,919  11/1973  Boswell et al. .................. 514/179
4,096,239   6/1978  Katz et al. ...................... 424/426
4,191,741   3/1980  Hudson et al. .................. 424/425

*Primary Examiner*—Leonard Schenkman
*Assistant Examiner*—Joseph A. Lipovsky
*Attorney, Agent, or Firm*—Alphonse R. Noë; H. G. Jackson

[57] ABSTRACT

The invention relates to biodegradable compositions which continuously release estradiol in a uniform manner over extended periods of time and do not exhibit initial release of undesirably high levels of active ingredient.

The invention also relates to a method for preparation of the compositions, and a method for administering estradiol parenterally to feedlot animals in a continuous and uniform fashion over extended periods of time.

11 Claims, No Drawings

ESTRADIOL IMPLANT COMPOSITION AND METHOD FOR PREPARATION

BACKGROUND OF THE INVENTION

Estradiol(17-beta-estradiol) is a naturally occurring estrogen which is frequently administered to ruminant animals to increase weight gains of the animals. To be effective for increasing weight gains in animals estradiol should be administered at a rate to provide about 50 to 70 micrograms/day/animal.

Feedlot animals are normally maintained at this treatment level for from about 120 days to about 210 days, thus an implant suitable for administration of estradiol should deliver about 50 to 70 micrograms/day/animal with a minimum of variation for up to 200 days without releasing excessive dosages or bursts which can lead to undesirable side effects.

Spherical implant pellets of estradiol having an inert core with the drug in a uniform biocompatable and biosoluble coating of cholesterol, solid polyethylene glycols, high molecular weight fatty acids and alcohols, biosoluble waxes, cellulose derivatives and solid polyvinyl pyrrolidone are described in U.S. Pat. No. 4,096,239.

Cylindrical implants which are not biodegradable, having an inert core which is 2 mm to 10 mm in diameter and 5 mm to 60 mm in length coated with a dimethylpolysiloxane coating, 0.2 mm to 1 mm thick containing 5% to 40% by weight of estradiol in the coating are disclosed in Lilly's U.S. Pat. No. 4,191,741 and their Australian Patent Application No. 476,747 describes improvements of this type of implant obtained by washing the implants and coating them with antibiotics or germacides.

Bioabsorbable compositions in particle or pellet form of polylactide-drug mixtures are disclosed in U.S. Pat. No. 3,773,919. The patent describes broadly pharmaceutical depot compositions designed to release effective amounts of drugs over a controlled period of time utilizing a biodegradable polylactide carrier or matrix or polyglycolide or a copolymer of lactide or glycolide containing up to 50% by weight of a comonomer in conjunction with a drug in drug to polymer ratios of from 1%/99% to 99%/1%. The patent also discloses ratios of estradiol to polymer as one part of drug to from 4 to 20 parts of polylactide i.e., from 5% to 25% by weight of estradiol.

It is an object of the invention to provide improved biodegradable compositions which release estradiol in a continuous fashion over extended periods of time and are suitable for parenteral administration to feedlot animals for increasing weight gains of animals. It is another object of this invention to provide improved compositions for administering estradiol parenterally to animals which do not initially or periodically release excessive, undesirable levels of the drug as well as a method for their preparation.

SUMMARY OF THE INVENTION

The invention is improved biodegradable implant compositions for parenteral administration which continuously release estradiol in animals in uniform fashion over extended periods of time comprising on a weight to weight basis 65% to 80% of estradiol and 20% to 35% of a biodegradable polymer of poly(lactide-co-glycolide) in ratios in a range of from 75/25 to 95/5. Preferred implant compositions of the invention are comprised on a weight basis of 70% to 80% of estradiol and 20% to 30% of a biodegradable poly(lactide-co-glycolide) polymer having a l-lactide/glycolide ratio of from 80/20 to 95/5. Compositions comprised on a weight basis of 70% to 75% estradiol and 25% to 30% poly(lactide-co-glycolide) polymer having a l-lactide/glycolide ratio of 90/10 are most preferred.

Implants about 2.4 mm in diameter and from 4 mm to 6 mm in length are the desired size to provide the required dosage for the entire treatment period.

The invention includes a method for preparing an implant with a porous, estradiol-free coating comprising washing the implant in a solvent in which estradiol is freely soluble for example, an alcohol, an ether or a ketone.

It has been found that while prior implant compositions for parenteral administration of estradiol contain on a weight basis a maximum of 50% by weight of the drug, highly effective implant compositions containing 65% to 80% by weight of estradiol may be prepared which do not exhibit erratic release or initial busts of undesirably high levels of estradiol. Due to the high estradiol content of the compositions of this invention, a single implant of about 2.4 mm in diameter and 4 mm to 6 mm in length can deliver 25 to 35 micrograms/day/animal in a continuous and uniform fashion for extended periods of time. The small size and potency of the estradiol implant compositions of the invention provide several advantages over currently available estradiol implant compositions which are either considerably larger and/or require multiple or repeated implantation in order to provide the required level of drug for extended periods of time. Initial administration to cattle of two of the implants of this invention are sufficient to provide the required 50 to 70 micrograms/animal/day for the entire treatment period.

The preferred levels of estradiol and lactide/glycolide ratios employed for the preparation of the compositions of this invention which contain these high levels of drug have demonstrated average release rates in animals in the 25 to 35 microgram/day range for from 110 to 200 days, while implants prepared with 50% estradiol and 50% polymer having a lactide/glycolide ratio of 70/30 showed a release rate in animals of 40 micrograms/day for only 63 days with a large increase in release rate thereafter.

Additionally, it has been found that the release rate of estradiol from implant compositions of this invention containing high levels of drug and a biodegradable l-lactide/glycolide polymer ratio as defined above may be controlled by washing the implant with a solvent in which estradiol is soluble such as methanol. Washed implants do not exhibit undesirable high levels of drug and additionally show a gradual increase to the required release rate over time as illustrated in Table I below. This table summarizes the differences in initial blood levels of estradiol in picograms/mL which are obtained by implanting an unwashed implant and a methanol washed implant containing estradiol in a weight range of 70–75% and l-lactide/glycolide polymer in a weight range of 25–30%, having a l-lactide/glycolide ratio of 90/10.

TABLE I

Serum estradiol concentrations
washed (A) vs unwashed (B) picogram/mL[1]

| Day | Washed implant A | Unwashed implant B |
|---|---|---|
| 0 | 6.6 | 10.2 |
| 2 | 15.8 | 56.6 |
| 5 | 21.1 | 59.9 |
| 8 | 37.3 | 110.8 |
| 12 | 22.0 | 108.3 |
| 14 | 36.1 | 63.4 |

[1] Average level of 5 animals

While washing of the implant compositions would be expected to remove estradiol from the surface, examination of the surface of implants of the invention containing high levels of drug with a biodegradable l-lactide/-glycolide polymer by Scanning Electron Microscopy, reveals that unwashed implants and polymer implants containing no drug have similar featureless surfaces. Examination of the surface of washed implant composition of the invention containing high levels of drug shows that it has developed fine pores, all of which are less than 20 micrometers in diameter and most of which are one micrometer or less, providing a porous membrane like surface to the implant. This resulting porous skin acts like a porous coating on the implant providing additional control in the release rate of the drug.

Solvents suitable for washing the implant compositions of this invention which are capable of providing this porous membrane-like layer on the surface include those solvents in which estradiol is freely soluble such as alcohols, ketones, ethers and the like, with methanol and ethanol being preferred.

The estradiol implant compositions may then be sterilized by optionally coating with an antibiotic such as oxytetracycline hydrochloride or by irradiation for example by exposure to gamma rays to aid in the prevention of infection at the site of administration.

Implant compositions of the invention may be prepared by dissolving the required quantity of a biodegradable l-lactide/glycolide polymer having the desired l-lactide to glycolide ratio in methylene chloride while stirring; adding the desired proportion of powdered estradiol to the stirred polymer solution; and then adding to the stirred mixture a miscible cosolvent in which the polymer is insoluble such as heptane to precipitate the polymer. The resulting solids are filtered off, and dried under reduced pressure. The resulting dry mixture is then ground and passed through a 20 mesh screen and the powder pressed to a preform tablet of approximate weight. Implants may then be prepared by tableting the powder at ambient temperatures or by molding the preform at elevated temperatures. The implants are then washed in a solvent in which estradiol is freely soluble for ten seconds followed by a second wash. The washed implants are then dried and if desired, may then be sterilized by irradiation for example with a cobalt-60 source or if desired be coated with an antibiotic such as oxytetracycline hydrochloride or equivalent.

The invention is further illustrated by the following non-limiting examples.

EXAMPLE 1-8

1. Polymer Synthesis

A mixture of l-lactide and glycolide in the desired ratio is heated to a melt under nitrogen. Stannous chloride dihydrate (catalyst) and diethylene glycol (initiator) are added and the mixture is stirred at high temperature (195°-208°). Upon completion of the reaction (about 90 minutes), the polymer is discharged, ground and vacuum dried to remove monomers.

2. Polymer Purification (optional)

The polymer is dissolved in methylene chloride and added slowly into methanol with good agitation. The precipitated polymer is then dried under vacuum at 40° C. to constant weight.

3. Mixing of Estradiol and Polymer a. Coacervation

The polymer is dissolved in methylene chloride and estradiol powder is added in the desired ratio to the polymer. Heptane is slowly added to the stirred mixture and after vigorous stirring, the solid mix is isolated by decantation or filtration and drying; or b. Wet Granulation The polymer is dissolved in methylene chloride and added to the stirred estradiol powder in a blade mixer. The solvent is removed after blending and the mixture is discharged.

4. Preform Tableting

The estradiol and polymer mixture is ground and put through a 20-mesh sieve. The powder is fed to a Stokes rotary press to make 7/16 inch tablets of appropriate weight.

5. Implant Molding

A multi-station mold and a 12.5 ton hydraulic press are used to fabricate the implants. The mold is heated by a circulating liquid system. The preforms are placed in the stations. The mold is then closed and a line pressure of 300-2000 psig applied, depending on the number of stations used and the polymer characteristics. The implants are released after opening the mold. They are removed.

6. Implant Washing

Implants are placed in a screen-bottomed basket and dipped into a methanol bath for ten seconds followed by a second methanol wash for five seconds. The washed implants are dried at ambient temperature.

7. Oxytetracycline Hydrochloride Dusting

Implants are placed in a container containing oxytetracycline hydrochloride, and are shaken for two minutes. The contents are poured over a sieve to remove the excess oxytetracycline hydrochloride and may then be stored or packaged.

8. Sterilization

The implants are packed in cartridges, wrapped and boxed and are irradiated using a cobalt-60 source at a nominal dosage of 2.5 megarads.

Utilizing the above procedure yields the implant compositions listed in Table II below.

TABLE II

| Composition | Estradiol implant compositions % by weight[1] | | | | | | | |
|---|---|---|---|---|---|---|---|---|
| | 1 | 2 | 3 | 4 | 5 | 6 | 7 | 8 |
| Polymer l-lactide-glycolide | 28 | 28 | 28 | 28 | 28 | 30 | 20 | 35 |
| (lactide/glycolide) | (95/5) | (90/10) | (85/15) | (80/20) | (70/30) | 90/10 | 90/10 | 90/10 |
| Estradiol | 72 | 72 | 72 | 72 | 72 | 70 | 80 | 65 |

[1]Rounded to the nearest whole number

EXAMPLE 9

Effect of washing implant compositions of the invention on initial release rate Estradiol implant compositions comprising approximately 70% estradiol and 30% of a polymer having a l-lactide/glycolide ratio of 90/10 are prepared by the general procedure of Examples 1–8. Ten of the implants are subjected to the washing procedure described in the above examples prior to coating with oxytetracycline hydrochloride (Group A), and ten are not washed but coated with oxytetracycline hydrochloride (Group B).

The implants are administered to the groups of five beef type steers (500–600 lbs each) of approximately equal weight, each animal receiving two implants washed (Group A) or unwashed (Group B) subcutaneously in the back of the ear. Animals are then maintained on a daily ration of hay and grain expected to produce a one pound per day weight gain per animal. Blood samples are obtained from each steer on day 0 (prior to administration) and on days 2, 5, 8, 12 and 14 thereafter. Each plasma sample is assayed by radio immune assay for estradiol 17 beta concentration and the results recorded.

The results of these experiments which are summarized in Table I below demonstrate improvement in the control of the initial release of estradiol 17 beta from the implant compositions of the invention.

TABLE I

| | Serum estradiol concentrations washed (A) vs unwashed (B) picogram/mL[1] | |
|---|---|---|
| Day | Washed implant A | Unwashed implant B |
| 0 | 6.6 | 10.2 |
| 2 | 15.8 | 56.6 |
| 5 | 21.1 | 59.9 |
| 8 | 37.3 | 110.8 |
| 12 | 22.0 | 108.3 |
| 14 | 36.1 | 63.4 |

[1]Average level of 5 animals

EXAMPLE 10

EFFICACY OF IMPLANT COMPOSITIONS OF THE INVENTION

Two estradiol implants weighing 27 mg each prepared as described in Examples 1–8 containing 70–75% estradiol and 25–30% of a polymer having an l-lactide/glycolide ratio of 90/10 which have been washed with methanol and coated with oxytetracycline hydrochloride are administered as described in Example 8 to each of three Hereford steers weighing approximately 500–600 pounds. The animals are maintained on a cattle growing ration which is introduced over a two week period to a rate of 5.0 kg/head/day along with 2.0 kg of mixed grass hay. Water is provided ad libitum.

Experimental Procedures

The test animals are weighed and acclimatized to their individual pens for ten days prior to the day of implantation.

Blood samples are taken from each steer on days −10, −4 and day 9 (just before implantation) to provide baseline information regarding serum estradiol 27 beta and blood urea nitrogen concentrations. On day 0, three animals received two estradiol implant each subcutaneously behind the the right ear while the single steer receives no implant and is maintained as an untreated control.

Additional blood samples are taken following implantation on days 7, 10, 14, 21, 28 and then every other week. Each of these samples is analyzed for estradiol 17 beta. Each animal is also weighed and has the implant site examined on these designated days for bleeding. Feed intake of the test animals is monitored throughout the duration of the trial.

The blood samples have the serum separated from the clot by centrifugation and samples are subjected to an RIA assay for estradiol 17 beta determination.

The results of these experiments are summarized in Table III below, which demonstrate the efficacy of the implant compositions of the invention in delivering uniform levels of estradiol in a continuous fashion for extended periods of time.

TABLE III

| | Estradiol picograms/mL in | |
|---|---|---|
| Day | Untreated control | Estradiol implant composition |
| −10 | <8.5 | <8.5 |
| −4 | <8.5 | <8.5 |
| 0 | <8.5 | <8.5 |
| 7 | <8.5 | 46.5 |
| 10 | <8.5 | 30.4 |
| 14 | <8.5 | 18.4 |
| 21 | <8.5 | 43.3 |
| 28 | <8.5 | 32.8 |
| 42 | 15.7 | 17.7 |
| 56 | 12.1 | 23.2 |
| 70 | <11.3 | 27.4 |
| 84 | <8.6 | 42.4 |
| 98 | <10.3 | 25.8 |
| 112 | <11.9 | 37.2 |
| 126 | <10.1 | 16.9 |
| 140 | <7.9 | 22.8 |

What is claimed is:

1. An improved biodegradable implant composition wherein the improvement comprises an implant containing on a weight basis 65% to 80% estradiol and 20% to 35% of a poly(lactide-co-glycolide) polymer having an l-lactide/glycolide ratio in a range of from 75/25 to 95/5 which has been washed with an alcohol, a ketone or an ether to provide a porous estradiol free coating having a pore size of less than twenty micrometers.

2. The composition according to claim 1 comprising 70% to 80% estradiol and 20% to 30% of a biodegradable poly(lactide-co-glycolide) polymer having an l-lactide/glycolide ratio in a range of from 80/20 to 95/5.

3. The composition according to claim 2 comprising 70% to 75% estradiol and 25% to 30% poly(lactide-co-glycolide) polymer having an l-lactide/glycolide ratio of 90/10.

4. An implant comprised of the composition according to claim 2 or 3 which is about 2.4 mm in diameter and from 4 mm to 6 mm in length.

5. The implant according to claim 4 which has been methanol washed to provide a porous estradiol free coating.

6. The implant according to claim 5 which is coated with oxytetracycline hydrochloride.

7. A method for administering estradiol in a continuous and uniform manner for extended periods of time comprising, implanting a biodegradable composition about 2.4 mm in diameter and about 4 mm to about 6 mm in length comprising on a weight basis 65% to 80% estradiol and 20% to 35% of a poly(lactide-co-glycolide) polymer having an l-lactide/glycolide ratio in a range of from 75/25 to 95/5 which has been washed with an alcohol, a ketone or an ether to provide a porous estradiol free coating having a pore size of less than twenty micrometers.

8. The method according to claim 7 wherein the composition comprises on a weight basis 70% to 80% estradiol and 20% to 30% of a poly(lactide-co-glycolide) polymer having an l-lactide/glycolide ratio of from 80/20 to 95/5; which is coated with oxytetracycline hydrochloride.

9. The method according to claim 8 in which the composition has been methanol washed.

10. A method for the preparation of a biodegradable estradiol implant composition, with a porous coating, of about 2.4 mm in diameter and from about 4 mm to about 6 mm in length containing on a weight basis from 65% to 80% estradiol and 20% to 35% of a poly(lactide-co-glycolide) polymer having an l-lactide/glycolide ratio in a range of from 75/25 to 95/5 comprising washing the implant in an alcohol, a ketone or an ether to provide a porous estradiol free coating having a pore size of less than twenty micrometers.

11. The method according to claim 10 wherein the implant is washed in methanol.

* * * * *